United States Patent [19]

Hanson et al.

[11] Patent Number: 4,824,786

[45] Date of Patent: Apr. 25, 1989

[54] METHYLOTROPH CLONING VEHICLE

[75] Inventors: Richard S. Hanson, Deephaven; Larry N. Allen, Excelsior, both of Minn.

[73] Assignee: The Regents of the University of Minnesota, Minneapolis, Minn.

[21] Appl. No.: 107,244

[22] Filed: Nov. 13, 1987

Related U.S. Application Data

[63] Continuation of Ser. No. 650,825, Sep. 14, 1984, abandoned.

[51] Int. Cl.[4] .................. C12N 1/20; C12N 15/00
[52] U.S. Cl. ..................... 435/252.3; 435/172.3; 435/320; 935/26; 935/29; 935/72; 536/27
[58] Field of Search .............. 435/172.3, 253, 320; 935/26, 29, 72

[56] References Cited

U.S. PATENT DOCUMENTS

| | | | |
|---|---|---|---|
| 3,663,370 | 5/1972 | Kono | 195/49 |
| 3,907,637 | 9/1975 | Nakayama | 195/29 |
| 3,963,572 | 6/1976 | Gatenbeck | 195/28 |

FOREIGN PATENT DOCUMENTS

29791/75 11/1980 Japan .

OTHER PUBLICATIONS

Haber et al. (1983), Science, 221:1147–1153.
Ditta et al. (1980), PNAS USA, 77:7347.
Friedman et al. (1982), Gene, 18:289.
Knauf et al. (1982), Plasmid, 8:45.
Holloway (1981), *Microbial Growth on C—1 Compounds,* H. Dalton Ed., London, pp. 317–324.
Rieb et al. (1980), Genet. Res., 36:99.
Bagdasarian et al. (1981), Gene, 16:237.
Gautier et al. (1980), Mol. Gen. Genet., 178:375.
Moore et al. (1983), J. Gen. Microbiol., 129:785–799.
Tatra et al. (1983), J. Gen. Microbiol., 129:2629–2632.
O'Connor et al. (1978), J. Gen. Microbiol., 104:105–111.
Warner et al. (1980), FEMS Microbiol. Letters, 7:181–185.
Jeyaseelan et al. (1979), FEMS Microbiol. Letters, 6:87–89.
Haber, 1984, "Plasmid DNA from an Obligate Methanetroph: Physical and Conjugative Characteristics", Ph.D. Dissertation, Univ. Wisc. Madison, pp. 128–156.
Gowrishankar et al. 1982, "Regulation of Phenylalanine Biosynthesis in *E. Coli* K—12 . . . ", J. Bact., v 150(3), pp. 1130–1137.
Toukdarian et al. (1984), Journal of Bacteriology, 157(3):979–983.
Suzuki et al. (1977), J. Ferment. Technol., 55(s):466–475.
Allen et al. (1984), Microbial Growth on C1 Compounds, Proc. 4th Int'l. Symp. Crawford, Ed.

*Primary Examiner*—Thomas G. Wiseman
*Assistant Examiner*—Thomas D. Mays

[57] ABSTRACT

A cloning vehicle comprising: a replication determinant effective for replicating the vehicle in a non-$C_1$-utilizing host and in a $C_1$-utilizing host; DNA effective to allow the vehicle to be mobilized from the non-$C_1$-utilizing host to the $C_1$-utilizing host; DNA providing resistance to two antibiotics to which the wild-type $C_1$-utilizing host is susceptible, each of the antibiotic resistance markers having a recognition site for a restriction endonuclease; a cos site; and a means for preventing replication in the $C_1$-utilizing host. The vehicle is used for complementation mapping as follows. DNA comprising a gene from the $C_1$-utilizing organism is inserted at the restriction nuclease recognition site, inactivating the antibiotic resistance marker at that site. The vehicle can then be used to form a cosmid structure to infect the non-$C_1$-utilizing (e.g., *E. coli*) host, and then conjugated with a selected $C_1$-utilizing mutant. Resistance to the other antibiotic by the mutant is a marker of the conjugation. Other phenotypical changes in the mutant, e.g., loss of an auxotrophic trait, is attributed to the $C_1$ gene. The vector is also used to inactivate genes whose protein products catalyze side reactions that divert compounds from a biosynthetic pathway to a desired product, thereby producing an organism that makes the desired product in higher yields.

3 Claims, 3 Drawing Sheets

↓ Hind III, Hpa I

↓ T4 DNA Polymerase

↓ T4 DNA Ligase

METHYLOTROPH CLONING VEHICLE

This invention was made with Government support under Contract No. (DE-AC02-82ER12029) awarded by the Department of energy. The Government has certain rights in this invention.

This is a continuation of co-pending application Ser. No. 650,825 filed on 9/14/84 abandoned.

BACKGROUND OF THE INVENTION

This invention relates to cloning vehicles and methods for engineering $C_1$-utilizing microorganisms producing a desired compound; it also relates to the resulting engineered microorganisms.

In theory, organisms that use $C_1$ compounds as a source of carbon and energy should be useful for fermentation processes producing desired compounds, because $C_1$ compounds such as methanol are relatively cheap and available. There are various disclosures of fermentation processes based on $C_1$-utilizing organisms. For example, Kono U.S. Pat. No. 3,663,370 discloses synthesizing glutamic acid using specific strains of Methanomonas, Protaminobacter, and Microcyclus. Nakayama U.S. Pat. No. 3,907,637 discloses synthesizing L-lysine by fermentation of a mutant Protaminobacter capable of utilizing methanol. Gatenback U.S. Pat. No. 3,963,572 discloses synthesizing L-tryptophan from indole or derivatives thereof using Pseudomonas AM 1 or Methylomonas methanolica, in which methanol is the primary source of carbon. Kiyoshi et al. (1975) Jap. Appl'n No. 29721/75 discloses synthesizing L-tryptophan using mutants derived from the genera Pseudomonas, Methanomonas, or Protaminobacter.

It is desirable to engineer organisms to improve product yield; however, engineering $C_1$-utilizing microorganisms is generally difficult because their genomes are relatively poorly characterized compared to organisms such as E. coli, and it is difficult to isolate stable mutants. Moreover, engineering $C_1$-utilizers is also difficult because of the lack of vehicles that directly transform $C_1$-utilizers; thus it is difficult to develop efficient gene transfer systems for $C_1$-utilizers. Finally, antibiotic resistance characteristics of $C_1$-utilizing microorganisms may not be compatible with many common marker genes used in engineering procedures, such as genes for resistance to trimethoprin, streptomycin, or ampicillin.

Various efforts have been made to study the genome of $C_1$-utilizing microorganisms using genetic engineering techniques. Haber et al. (1983) Science 221:1147-1153 reviews a number of articles including methods for transferring cloned DNA into methylotrophs using conjugative or mobilizable cloning vectors. The former are transferred between bacterial cells by simple mating techniques, and the latter are transferred only with the assistance of another mobilizing plasmid that codes for the gene products necessary for conjugal transfer. Those vectors include:

(1) pRK290, a mobilizable plasmid derived from RK2 (a broad host range plasmid); pRK290 contains genes coding for resistance to three antibiotics including tetracycline; it is mobilized to transfer by conjugation between E. coli and various other strains in the presence of helper plasmid pRK2013 [Ditta et al. (1980) PNAS USA 77:7347];

(2) pLAFR1 is a mobilizable cosmid derivative of pRK290 containing a gene for tetracycline resistance; pLAFR1 cosmids are mobilized from Rhizobium meliloti into E. coli and back again in the presence of helper plasmid pRK2013 [Friedman et al. (1982) Gene 18:289];

(3) pVK100, pVK101, and pVK102 are mobilizable derivatives of pRK290 containing a kanamycin resistance gene from plasmid R6-5; pVK102 is a cosmid vector having cloning sites in resistance genes that allow selection for inserts [Knauf et al. (1982) Plasmid 8:45];

(4) R68.45 is a conjugative plasmid with a broad host range; it is mobilizable to transfer between E. coli and Pseudomonas aeruginosa, Pseudomonas AM1, Methylosinus trichosporium OB36, and Methylobacterium organophilum xx [Holloway (1981) Microbial Growth on C-1 Compounds, H. Dalton Ed., London p. 317].

(5) pM061 is a conjugative plasmid derived from R68.45 with enhanced chromosomal mobilization host range and [stability of R' plasmid derivatives - ? in article]. Transfer frequencies reportedly are similar to R68.45 [Reiss et al. (1980) Genet. Res. 36:99];

(6) RSF1010 is a mobilizable plasmid having a broad host range that transfers between E. coli and Pseudomonas AM1 [Bagdasarian et al. (1981) Gene 16:237; Gautier et al. (1980) Mol. Gen. Genet. 178:375]; and (7) pKT230 and pKT231 are mobilizable derivatives of RSF1010 containing cloning sites in resistance genes to allow selection for inserts [Bagdasarian (1981), cited above].

Moore et al. (9183) J. Gen. Microbiol. 129:785-799 disclose a method of complementation mapping of Methylophilus methylotrophus using a plasmid that is an $R^1$ derivative of plasmid pM0172.

Gautier et al. (1980) Mol. and Gen. Genetics 144:243-251 disclose cloning the wild-type methanol dehydrogenase gene of Psuedomonas AM 1 in E. coli using plasmid R1162. The methanol dehydrogenase gene is then transferred to a methanol dehydrogenase mutant of Pseudomonas AM 1 using RP4 to mobilize the hybrid plasmid.

O'Connor et al. (1978) J. Gen. Microbiol. 104:105-111 disclose transforming Methylobacterium organophilum in order to study the linkage of $C_1$-utilizing genes in that organism.

Warner et al. (1980) FEMS Microbiol. Letters 7:181-185 and Jeyaseelan et al. (1979) FEMS Microbiol. Letters 6:87-89 disclose an attempt to use a broad host-range plasmid, R68.45, to map chromosomes of several genera of $C_1$-utilizing organisms.

Tatra et al. (1983) J. Gen Microbiol. 129:2629-2632 disclose that R68.45, referred to above, can mobilize the chromosome of Pseudomonas AM 1. Markers are linked to genes to demonstrate their location.

SUMMARY OF THE INVENTION

We have discovered versatile cosmid cloning vehicles that can be used generally to characterize and engineer the genome of $C_1$-utilizing microorganisms. The vehicles have a broad host range and can transfer by conjugation between a non-$C_1$-utilizing host and a $C_1$-utilizing host so that complementation mapping can be used to characterize the genome of the $C_1$-utilizing organism, and having done so, to engineer selected genes to increase production of desired compounds by the $C_1$-utilizing organism.

By the term $C_1$-utilizing microorganisms, we mean to include all organisms that can use as a carbon/energy source $C_1$ compounds such as methane or methanol. We specifically mean to include facultative and obligate $C_1$-utilizing microorganisms; methane and methanol-utilizing microorganisms; and type I (i.e. those using the ribulose monophosphase pathway) and type 2 (i.e. those using the serine pathway) microorganisms. The term also includes bacteria as well as yeast or other $C_1$-utilizing microorganisms. For a general discussion of classification of $C_1$-utilizing microorganisms, see Haber et al. (1983) Science 221:1147–1153 and references cited therein. References herein to genus and species refer to organisms as classified in Buchanan et al., The Shorter Bergey's Manual For Determinative Bacteriology (Williams & Wilkins, 1982).

In a first aspect, the invention generally features a cloning vehicle comprising: a replication determinant effective for replications the vehicle in a non-$C_1$-utilizing host and in a $C_1$-utilizing host; DNA effective to allow the vector to be mobilized from the non-$C_1$utilizing host to the $C_1$utilizing host; DNA providing resistance to at least two antibiotics to which the wild-type non-$C_1$-utilizing host is susceptible, at least one of the antibiotic resistance markers having a recognition site for a restriction endonuclease that generates fragments that are ligatable to DNA digested by a restriction endonuclease that recognizes sites consisting of four nucleotides or less; and a cos site.

The vehicle is capable of: (1) receiving, at the restriction nuclease recognition site, an insertion of DNA comprising a gene-containing fragment of the digested genome of the $C_1$-utilizing organism, thereby inactivating resistance to one of the antibiotics as a marker of the insertion; (2) forming a cosmid structure; (3) infecting the non-$C_1$-utilizing host; and (4) conjugating with a mutant of the $C_1$-utilizing host that is mutated in the gene, whereby the gene-containing fragment vehicle complements the mutant, thus signaling the function of the gene.

In preferred embodiments, the replication determinant is a replicon such as the one reported in pRK290; the antibiotic resistance is to kanamycin or tetracycline; the cos site is from phage lambda; the DNA effective to allow the vehicle to be mobilized is derived from pRK290; the mobilizing plasmid is pRK2913; the $C_1$-genome-digesting restriction endonuclease is Sau3A; the vehicle is selected from pLA2901, pLA2905, pLA2910, and pLA2917; and the internal recognition site of the first antibiotic resistance gene is BglII or Sau3A.

In a second aspect, the invention features using the above-described vehicle for complementation mapping of a $C_1$-utilizing organism by: digesting the genome of the $C_1$-utilizing organism with a restriction endonuclease that recognizes a 4-nucleotide base-pair sequence to generate gene-containing fragments; inserting one of the gene-containing fragments into the recognition site of the internal antibiotic resistance gene of the vehicle to inactivate the resistance, packaging the gene fragment-containing vehicle into a cosmid structure; infecting a non-$C_1$-utilizing host; selecting the infected non-$C_1$-utilizers from a heterorgeneous population that are resistant to the second but not the first antibiotic; mobilizing the gene fragment-containing vehicle from the selected non-$C_1$-utilizing host into a $C_1$-utilizing host that is mutated in the gene of interest; and determining whether the gene fragment-containing vehicle complements the mutant and therefore whether the vehicle contains the gene of interest.

In preferred embodiments of the second aspect of the invention, the gene of interest is a gene expressing an enzyme of an aromatic amino acid synthesis pathway; the vehicle is pLA2901, pLA2905, pLA2910, or pLA2917; and the $C_1$-utilizing organism is *Methylobacterium organophilum*.

The above-described vehicle is particularly useful for characterizing the genome of the $C_1$-utilizer by transferring those genes to a mutant $C_1$-utilizer or to a non-$C_1$-utilizer and performing complementation mapping. Specifically, the cosmid will harbor coding capacity sufficient such that after digesting the $C_1$-utilizer chromosome and packaging the segments, the phage particles used to infect the non-$C_1$-utilizing host, specifically E. coli, include a complete representation of the host chromosome. Inserts are identified by loss of resistance, and complementation mapping allows pairing of specific changes in genome to specific phenotypical traits.

Having locating and cloned the gene coding for a target enzyme, it is possible to inactivate that enzyme by engineering the gene in the non-$C_1$-utilizing host. Specifically, a transposon is inserted in the gene, and the engineered gene is returned to the $C_1$-utilizing host where it replaces the wild-type gene on the chromosome by homologous recombination. The $C_1$-utilizer gene product is thus inactivated. By inactivating enzymes catalyzing undesired side reactions, yield of the desired compound is increased.

Thus, a third aspect of the invention features a vehicle for integrating DNA in the chromosome of a $C_1$-utilizer, which includes a homologous chromosomal fragment containing the transposon, as well as the above-described replication and mobilization enabling elements of the cosmid vehicle. In preferred embodiments, the vehicle further includes a means of preventing replication in the $C_1$-utilizing host including a temperature sensitive repressor; and the transposon is Tn5.

In a fourth aspect, the invention features a $C_1$-utilizing microorganism having such an engineered gene integrated in its chromosome. In preferred embodiments, the organism is a facultative methanol utilizer such as a *Methylobacterium organophilum*. The desired compound is an aromatic amino acid, e.g., phenylalanine, tyrosine, or tryptophan, and the undesired side pathways that are blocked involve synthesis of other aromatic amino acids. For example, the desired product is L-phenylalanine and the blocked side pathway steps include conversion of prephenate to p-hydroxyphenylpyruvate and conversion of chorismate to anthranilate.

In a fifth aspect, the invention features producing a desired compound by culturing a $C_1$-utilizing microorganism as described above.

Finally, the invention features a method of engineering a $C_1$-utilizing microorganism by identifying the gene to be engineered, transferring the gene to be engineered to a non-$C_1$-utilizer altering the gene by inserting a site-directed transposon therein, and transferring the altered gene to a $C_1$-utilizing microorganism where it integrates in the chromosome.

Other features and advantages of the invention will appear from the following description of the preferred embodiment and from the claims.

DESCRIPTION OF THE PREFERRED EMBODIMENT

We turn now to a description of the preferred embodiment of the invention, first briefly describing the drawings.

Figure 1:
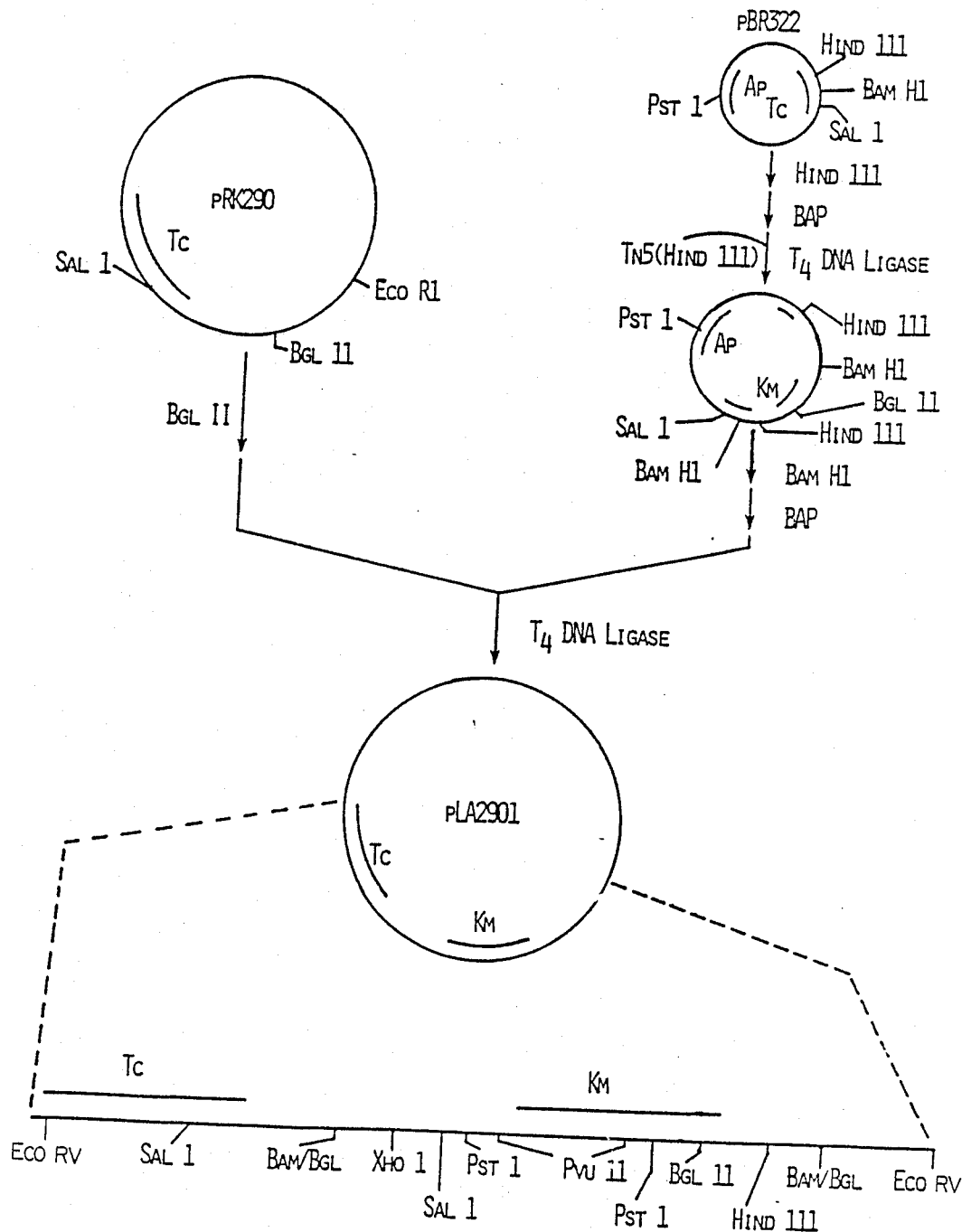
FIG. 1 is a flow diagram of a process for producing the cloning vector pLA2901.

The preferred cloning vehicles are illustrated by the following descriptions of specific vehicles denoted pLA2920, pLA2905, pLA2910, and pLA2917; the two most preferred vehicles are pLA2917 and pLA2920. The latter two vehicles have been deposited with the American Type Culture Collection and given accession nos. 39840 and 39841, respectively. Applicants recognize their obligation to notify the ATCC of the issuance of a patent on this application, to make the above deposits publicly available thereafter, and to replace the deposit should it die during the effectiveness of any patent issuing on this application.

We will describe first the construction of pLA2917 and the derivation of pLA2920 from it, thereby providing a detailed description of the elements of thos plasmids.

We will then describe complementation analysis using those plasmids to characterize the genome of a $C_1$-utilizing microorganism, exemplified by a strain of *Methylobacterium organophilum*; we then will describe engineering selected genes of the $C_1$-utilizing microorganism and integration of those genes in the chromosome of that or another $C_1$-utilizing microorganism.

Finally, we will describe production of a desired product, exemplified by production of L-phenylalanine, by culturing the engineered $C_1$-utilizing microorganism on a $C_1$ carbon source.

GENERAL TECHNIQUES

Except as noted below or as noted elsewhere in this application, the experimental techniques that can be used to accomplish the engineering described in this application are described in Maniatis *Molecular Cloning*, Cold Spring Harbor Laboratory, 1983.

*Escherichia coli* is routinely cultured on LB medium as described in Miller (1972) Experiments in Molecular Genetics, P. 433 (Cold Spring Harbor Laboratory, Cold Spring Harbor, N.Y.). Unless otherwise specified, *M. organophilum* ATCC 27886, *M. organophilum* DSM 760, and Ps. AM 1 strains are grown on MacLennan salts (see Maclennan et al. (1971) J. Gen. Microbiol. 69:395–404) supplemented with sodium succinate (0.1% weight/vol.) or methanol (0.5% vol/vol).

Antibiotics, when added, are used at final concentrations of 25 µg/ml (kanamycin) and 20 µg/ml (tetracycline) for *E. coli* and 10 µg/ml each for methylotrophs.

Preparative amounts of plasmid DNA are isolated from *E. coli* HB101 essentially by the method of Birnboim (1983) Methods Enzymol. 100:243–255. Cells are lysed in alkaline SDS followed by high salt precipitation. This material is centrifuged (8,000 rpm, 30 minutes) and the plasmid DNA is precipitated by the addition of 0.55 vol of col isopropanol. Plasmid DNA is then further purified by banding twice in ethidium bromide/CsCl dye bouyant density gradients.

Plasmid DNA from recombinant clones is screened by the miniprep procedure of Crosa et. al. ["Plasmids" (pp. 266–282) *Manual Of Methods for General Biochemistry*, Gerhardt e., Am. Soc. Microbiol. Wash, D.C., 1981] except that following isopropanol precipitation, restrictable plasmid preps are obtained by two successive precipitations with ethanol. Chromosomal DNA from wild-type strain xx is purified from cells lysed in the following manner. A late log phase culture of *M. organophilum* grown on Penassay broth is harvested by centrifugation (8,000 rpm, 10 minutes) and washed once by centrifugation with 1 M NaCl. The pellet is resuspended in 1 M NaCl (20 ml/gm wet weight) and incubated at 55° C. for 30 minutes. EDTA (ethylenediaminetetraacetate) is added to 0.1 M and the incubation at 55° C. is continued for 15 minutes. Cells are collected by centrifugation (8,000 rpm, 10 minutes) and resuspended in TES (10 nM TRIS(hydroxymethyl-amino methane)-HCl pH 8.0, 1 mM EDTA, 0.15 M NaCl) plus 10 mg/ml lysozyme. The cell suspensions are incubated at 37° C. for 45 minutes followed by the addition of sodium dodecyl sulfate (SDS) to 1% (wt/vol). After addition of SDS, the cells are incubated for 45 minutes at 65° C. Chromosomal DNA from cells lysed in the manner described above is purified by the method of Marmur (1961) J. Mol. Biol. 3:208–218.

Where indicated, DNA is purified from agarose gels by electroelution onto dialysis membranes according to the method of Yang et al (1979) Methods Enzymol. 68:176–182.

Restriction endonucleases are used according to manufacturers' recommedations (Bethesda Research Laboratories (BRL), Rockvill, MD and Promega Biotech Inc., Madison, Wisc.).

Nuclease Bal31 (BRL) is incubated with DNA at 0.09 units/µg DNA (500 µl) at 32° C. in 20 mM TRIS-HCl pH 8.0, 12 mM $CaCl_2$, 12 mM $MgCl_2$, 1 mM EDTA, 200 mM NaCl and 250 µg/ml BSA. Samples (22µl) are taken at regular intervals and the reaction stopped by the addition of 2 µl of 200 mM ethylene glycol-bis(B-amino ethyl ether)-N,N'-tetracetate(EGTA).

$T_4$ DNA polymerase (BRL) and deoxynucleotide triphosphates are used to generate blunt ends in Bal31 treated molecules. $T_4$ DNA ligase (Promega Biotech, Inc.) and Bacterial Alkaline Phosphatase (BRL) are used according to manufacturers' recommendations.

Bateriophage lamgda packaging extracts and in vitro packaging is performed by the method of Hohns (1979) Methods Enzymol. 68:299–309 as modified by Ostrow et al. (1983) J. of Invest. Dermatol. 80:436–440.

THE VEHICLES

Figure 2:
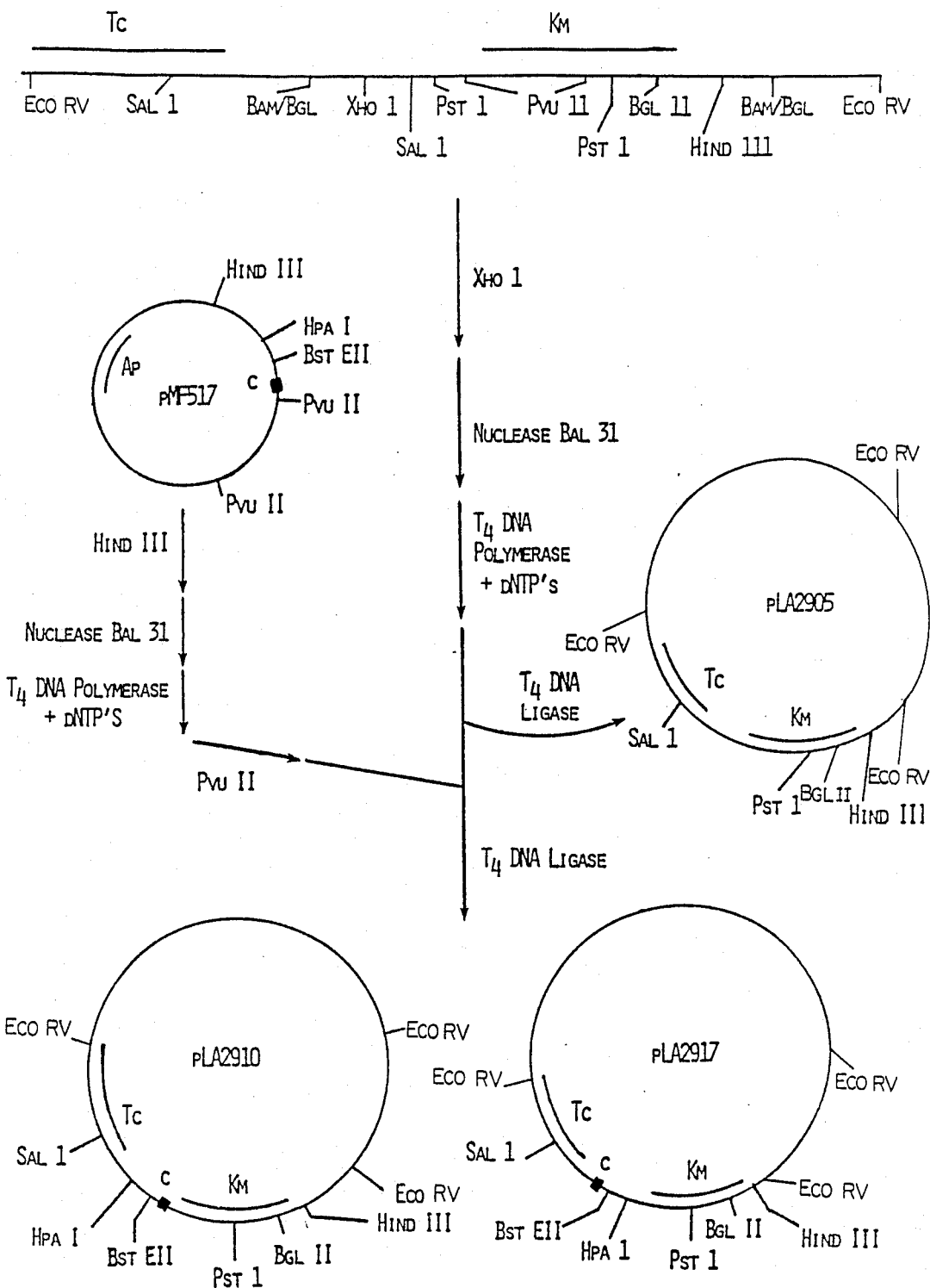
FIG. 2 is a flow diagram of a process for producing the cloning vectors pLA2905, pLA2910, and pLA2917.

FIG. 1 outlines the steps in the construction of pLA2901 from pRK290, which is then modified as shown in FIG. 2 to yield pLA2905, pLA2910, and pLA2917.

Figure 3:
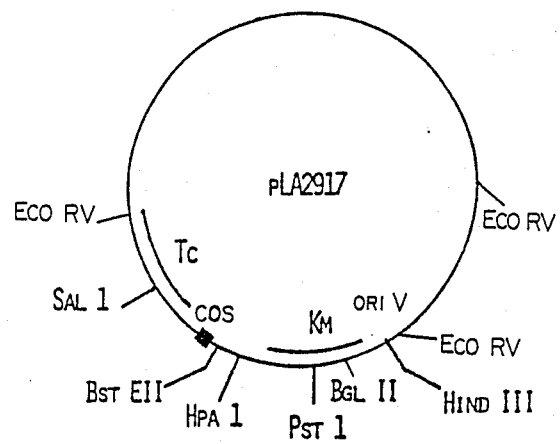
FIG. 3 is a flow diagram of a process for producing the cloning vector pLA2920.
Figure 3:
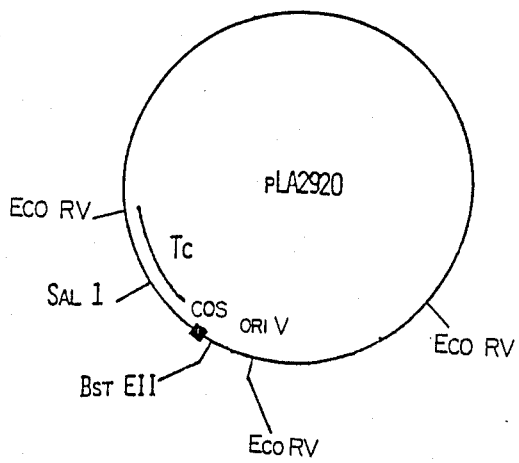

FIG. 3 outlines the steps in forming pLA2920 from pLA2917.

Plasmid pLA2917 is based on the broad host range mobile cloning vector pRK290 reported by Ditta et al. PNAS USA 77:7347–7351. pRK290 is a 20 kbp plasmid that can be mobilized from *E. coli* to several gram negative bacteria by RK2-derived plasmid pRK2013. Specifically, pLA2917 and pLA2920 include the kanamycin resistance gene of the Tn5 transposon, described below.

In order to incorporate the kanamycin resistance element of Tn5 into pRK290, pBR322 is digested with HindIII, and the HindIII fragment of transposon Tn5 is cloned into pBR322.

Next the kanamycin resistance element is excised from the resulting plasmid with BamHl. This element is inserted into pRK290 [Ditta et al. (1980) PNAS USA 77:7347–7351] by a BamHl/BglII fusion to yield a 22.4 kbp plasmid, pLA2901.

Plasmid pLA2901 harbors genes coding for resistance to kanamycin and tetracycline. It contains 5 unique restriction sites: the EcoRl site of pRK290, the HindIII site of pBR322, and the BglII, BstEII, and XhoI sites of Tn5. DNA insertions at the unique BglII site can be detected by inactivation of Km resistance.

More versatile cosmid vectors, pLA2910 and pLA2917, are then constructed from pLA2901 in the following manner. In order to generate unique restriction sites for PstI and SalI, pLA2901 is linearized with XhoI and treated with Ba131 Nuclease. The extent of Ba131 digestion is followed by subcutting samples at 2 minute intervals with PvuII and monitoring the PvuII fragment (originally 730 bp) of Tn5 on 4% polyacrylamide gels according to the method of Rothstein et al. (1980) Cell 19:795–805. An increase in the mobility (decrease in size) of this fragment indicates that Ba131 activity has proceeded past the SalI and adjacent PstI sites and into the region of the PvuII fragment.

The cohesive ends (cos site) of bacteriophage lambda are then introduced in order to generate a vector with increased DNA insert capacity. The origin of the lambda cos site in pLA2910 and pLA2917 is pMF517 disclosed by Feiss et al. (1972) Gene 17:123–130. This plasmid is linearized with HindIII, treated with Nuclease Ba131 to reduce the size of the resulting cos fragment by approximately 800 bp, and blunt ends are generated with T4 DNA polymerase plus dNTP's. The resulting DNA is subcut with PvuII, separated on a 0.7% agarose gel and the gel-purified cos fragment is ligated to pLA2901 which is treated as described above.

Cosmid pLa2917 is shown in FIG. 2; cosmid pLA2910 is the same as pLA2917, except that the lambda cos fragment is in the opposite orientation. The cos site allows in vitro packaging into bacteriophage lambda of inserts up to 30 kbp in length. Cosmid pLA2917 (21 kbp) contains 6 unique restriction enzyme cleavage sites: BglII, (Km), BstEII, HindIII, HpaI, PstI, (Km), and SalI (Tc). Several possible cassettes exist for the Km resistance gene. For example, a PhaI, EcoRV fragment of 1.4 kbp contains unique restriction sites for BglII, HindIII and PstI.

Plasmid pLA2920 is created from pLA2917 by deleting the kanamycin resistance segment to avoid internal rearrangement when the transposon segment moves and to permit selection of conjugants that have a Tn5 insertion. To construction pLA2920 from pLA2917, the latter was treated with HindIII and HpaI, and then with phage T4 DNA polymerase and the resulting strand was ligated as shown in FIG. 3.

The above-described vectors carry resistance determinants for kanamycin and/or tetracycline and have multiple unique restriction endonuclease cleavage sites. Insertional inactivation of kanamycin (BglII and PstI) and tetracycline (SalI) can be used to detect inserts. These vectors can transfer efficiently to a broad host range including *E. coli* HB101, *M. organophilum* strain xx, *M. organophilum* DSM 761. *Pseudomonas* AM 1, *Pseudomonas putida* and *Pseudomonas aeruginosa*. The previously described pVK100 series cosmids also have multiple drug resistance markers; however, the cosmids described here have the additional advantage of utilizing Sau3A generated partials of insert DNA to clone into the BglII site. The tetranucleotide recognition sequence of Sau3A allows the cloning of a more complete random set of partial digestion products than does a restriction endonuclease with a hexanucleotide recognition sequence. Indeed, examples of BglII or Sau3A inserts greater than 26 kbps with no internal sites for BglII and/or HindIII have been found in this laboratory. These libraries would not contain the entire genome.

CHARACTERIZATION OF THE $C_1$ UTILIZER'S GENOME

A $C_1$-utilizing organism is selected to be transformed to the ultimate fermentation host. For example, a strain of *Methylobacterium organophilum* (ATCC 27886), a facultative methlylotroph that prefers methanol as a carbon and energy source, is a suitable starting strain. Other suitable organisms include *Methylophilus methylotrophus*, *Pseudomonas aeruginosa* mutants, Pseudomonas AM 1, *Methylobacterium organophilum* DSM761, and *Pseudomonas putida*.

Once the ultimate fermentation host has been selected, its genome can be mapped and characterized to enable engineering that will enhance further the yield of the desired compound. Such complementation mapping is illustrated by the following description of mapping *M. organophilum*.

*M. organophilum* is naturally resistant to trimethoprin (100 µg/ml), mutates spontaneously at high frequency to streptomycin resistance, and due to the extended period necessary to select transconjugants (10–12 days), ampicillin is not sufficiently stable to allow selection of resistant colonies. As a result, these three antibiotics, frequently used for selection in genetic studies of other gram negative bacteria, cannot be used with this organism. *M. organophilum* strain xx is very sensitive (<10 µg/ml) to kanamycin and a convenient source of this antibiotic resistance determinant is the neomycin phosphotransferase gene of Tn5 as described by Beck et al. (1982) Gene 19:326–336. These factors, in addition to convenient restriction enzyme cleavage sites available for the isolation of this gene, are desirable factors.

A genomic library of *M. organophioum* strain xx DNA is constructed in the BglII site of pLA2917. A Sau3A partial digest of strain xx chromosomal DNA is size fractionated on a 0.5% agarose gel (500 ml) and partial digestion products ranging from 22 to 30 kbp are isolated. pLA2917 is linearized with BglII, treated with bacterial alkaline phosphatase, mixed with the *M. organophilum* strain xx DNA fragments, and the DNA mixture is treated with DNA ligase. Vector and chromosomal DNA are ligated at a vector-to-insert ratio of 2:1 and a total DNA concentration of 300 µg/ml. The ligation mixture is packaged into bacteriophage lambda and the resulting phage particles are used to infect *E. coli* HB101 (ATCC No. 33694). Several thousand transfectants can be obtained, and 2,000 are picked for further study. Tc$^R$ clones contain insert DNA with an average size of 28 kbp.

Complementation assays can be performed by patch plate matings. Fifty recombinant *E. coli* HB101 donors containing pLA2917 with inserts, arranged in a grid pattern on a master plate, can be replica plated onto a lawn of *E. coli* HB101 (pRK2013) and a *Ps. aeruginosa* auxotroph. Matings are incubated at 37° C. for nin hours and then replica plated onto selective media. In this way, mutant clones exhibiting a particular phenotypical trait (such as auxotraphes for some, but not all, aromatic amino acids) are complemented by specific clones containing specific recombinant plasmids, thus enabling identifications and mapping of the gene responsible for that trait.

Thus, the ability of recombinant molecules to complement mutants unable to grow without an amino acid is determined by patch plate matings. Plates are examined and donors are scored for the ability to complement markers in the recipients i.e., to restore ability to grow without the amino acid.

DNA from complementing clones is subcloned into pLA2920 and mutagenized in vivo with Tn5 in *E. coli* HB101 as described below. Since Tn5 does not appear to transpose in *M. organophilum,* these can be mobilized into strain xx wild type to create mutants by marker exchange. This establishes which functions are coded for by each cloned fragment and enables determination of linkages between other C-1 markers in *M. organophilum* strain xx.

ENGINEERING THE $C_1$-UTILIZING HOST

Where production of a specific compound is desired, mutants of the organism that are resistant to analogs of the product can be selected. For example, where phenylalanine production is sought, the original Methylotrophs are mutated chemically (for example, with N-nitrosoguanidine) and the mutants are exposed to 5-fluorophenylalanine. Resistant mutants such as ATCC No. 39866 are selected.

Having identified and cloned a gene for a side reaction which lessens product yield as described above, that gene can be rendered inactive as follows.

A plasmid such as pLA2920 containing the gene of interest is inserted into *E. coli* and is mutagenized by transposition of Tn5, a discrete 5.7 kilobase segment of bacterial DNA which can insert at high frequency into numerous sites in gram negative bacteria. It encodes resistance to kanamycin and neomycin in bacteria. Tn5 is disclosed in Berg et al. Bio/Technology July, 1983, pp. 417-435. A suitable source of Tn5 is plasmid pJBJI reported by Beringer et al. (1978) Nature 276:633-634. The transposon can move to new locations in DNA molecules without relying on extensive DNA sequence homology between the inserted element and the insertion site, and without relying on rec genes needed for classical homologous crossing over. That transposition is marked by an antibiotic resistance marker on Tn5 transposon plasmid. By restriction mapping techniques, it is possible to select events in which the transposon has inserted into the gene of interest.

The selected *E. coli* organisms are then conjugated with the ultimate $C_1$-utilizing host, and the gene of interest containing the inactivating insert integrates into the chromosome to replace the wild-type active gene.

In this way, genes whose protein products catalyze undesired side reactions are inactivated. The resulting $C_1$-utilizing organism provides enhanced yields of desired compounds.

FERMENTATION

The engineered $C_1$-utilizing microorganism may be cultured according to known techniques using a $C_1$ compound, preferably methanol as the primary source of carbon and energy. The desired compound is harvested according to known techniques. For example, the fermentation conditions described at p. 1089 in Demain at al. (1981) Appl. and Env. Microbiol 41:1088-1096 may be used, and the product recovery technique described at p. 777 in Yamada et al. (1981) Appl. and Env. Microbiol 42:773-778 may be used.

OTHER EMBODIMENTS

Other embodiments are within the following claims. For example, other transposons, other antibiotic resistance traits, and other replicons may be used. Similarly, other $C_1$-utilizing organisms may be used, and other desired compounds may be produced.

What is claimed is:

1. A cloning vehicle selected from the group consisting of the following plasmids: pLA 2917 as deposited in *E. coli* strain HB101 as ATCC 39840; pLA 2920 as deposited in *E. coli* strain HB101 as ATCC 39841; pLA 2901; pLA 2905; pLA 2910; and derivatives engineered therefrom.

2. A $C_1$-utilizing microorganism of the species *Methylobacterium organophilium,* the species *Pseudomonas aeruginosa,* or the strain Pseudomonas AM 1, and wherein said microorganism comprising a cloning vehicle selected from the group consisting of the following plasmids; pLA 2917 as deposited in *E. coli* strain HB101 as ATCC 39840; pLA 2920 as (deposited in *E. coli* strain HB101 as ATCC 39841; pLA 2901; pLA 2905; pLA 2910; and derivatives engineered therefrom.

3. The microorganism of claim 2 wherein said microorganism is *Methylobacterium organophilum* deposited as ATCC 39866 or a derivative thereof.

* * * * *